United States Patent [19]
Dixon et al.

[11] Patent Number: 5,381,224
[45] Date of Patent: Jan. 10, 1995

[54] SCANNING LASER IMAGING SYSTEM

[75] Inventors: Arthur E. Dixon, Waterloo, Canada; Savvas Damaskinos, Kitchener, Canada

[73] Assignee: A. E. Dixon, Waterloo, Canada

[21] Appl. No.: 113,172

[22] Filed: Aug. 30, 1993

[51] Int. Cl.⁶ .......................................... G01N 21/64
[52] U.S. Cl. ..................................... 356/72; 356/318; 356/417; 356/73; 250/458.1
[58] Field of Search .................. 356/73, 72, 317, 318, 356/417, 446; 250/458.1, 459.1, 461.1, 461.2

[56] References Cited

U.S. PATENT DOCUMENTS

| | | | |
|---|---|---|---|
| 5,091,652 | 2/1992 | Mathies et al. | 250/458.1 |
| 5,127,730 | 7/1992 | Brelje et al. | 250/458.1 |
| 5,274,240 | 12/1993 | Mathies et al. | 250/458.1 |
| 5,296,703 | 3/1994 | Tsien et al. | 356/318 |
| 5,304,810 | 4/1994 | Amos | 250/458.1 |

FOREIGN PATENT DOCUMENTS 92184829  1/1992  United Kingdom .

OTHER PUBLICATIONS

Cox, I. J., "Scanning Optical Fluorescence Microscopy", Journal of Microscopy 133, 149-154 (1984).

*Primary Examiner*—F. L. Evans

[57] ABSTRACT

A scanning optical imaging or mapping system for macroscopic specimens is disclosed, which allows both confocal and non-confocal imaging to be performed in reflected light, photoluminescence, fluorescence and other contrast mechanisms. Several embodiments are disclosed, for use in photoluminescence mapping of semiconductor specimens, fluorescence scanning of gels used in gene sequencing, fingerprint detection, and other application areas.

17 Claims, 6 Drawing Sheets

SCANNING LASER IMAGING SYSTEM

TECHNICAL FIELD

This invention relates to the field of Scanning Laser Imaging Systems when used to image macroscopic specimens (i.e. specimens larger than those viewed through a microscope, which usually have a maximum size of 1 mm×1 mm), including systems used to form Photoluminescence (PL) maps of semiconductor specimens, or images of semiconductor specimens in which the contrast mechanisms include reflected light, transmitted light, scattered light, lifetimes, optical beam induced current or voltage, and others. This invention further relates to fluorescence (FL) images or maps of biological or other specimens, as well as reflected light images of these specimens. This invention further relates to fluorescent gel scanning for gene sequencing, and also to the detection of fingerprints.

BACKGROUND OF THE INVENTION:

Much of the background information for this invention was described in British Patent Application GB 92 18482.9 by A. E. Dixon and S. Damaskinos, entitled "Apparatus and Method for Scanning Laser Imaging of Macroscopic Specimens". That application describes prior art systems for both fluorescence and photoluminescence imaging of large specimens using scanning stage confocal and non-confocal laser microscopes, and using camera systems in which the whole specimen is illuminated and imaged at the same time.

One type of large fluorescent specimen mentioned in GB 9218482.9 is the fluorescent gels used in DNA mapping and sequencing. A confocal scanning-stage laser fluorescence microscope was first described by Cox[1], and the use of such a microscope to image fluorescent gels is described by Mathies and Peck in U.S. Pat. 5,091,652. Although this method has good spatial resolution, it is slow since the large fluorescent gels must be translated under the fixed laser beam, and the scan speed is limited by the speed of the moving stages.

[1]. Cox, I. J. "Scanning optical fluorescence microscopy", Journal of Microscopy 133, 149–154 (1984).

In GB 9218482.9, Dixon and Damaskinos disclosed several embodiments of a scanning beam imaging system using a laser scan lens to focus the incoming laser beam onto the specimen, and then using the same lens to collect the reflected light (or photoluminescence or fluorescence) returning from the specimen. Most laser scan lenses are designed to give a constant scan velocity on the focal plane when the angle of deflection (theta) of the incident beam is varied at a constant rate. Such lenses are called F Theta lenses, and the image height is proportional to f*theta, whereas the image height of an ordinary photographic objective, or of a microscope objective, is f*tan(theta). Here theta is the angle between the incoming beam and the optic axis of the scan lens (the scan angle), f is the focal length of the laser scan lens, and * denotes multiplication. Some laser scan lenses are telecentric, i.e. they are made in such a way that the cone of light converging toward focus at a spot in the focal plane is perpendicular to the focal plane for all scan angles.

One embodiment of the scanning beam imaging system disclosed in GB 9218482.9 is shown in FIG. 1. Light beam 103 from laser 102 (or other light source) is focused on pinhole 106 by lens 104. The expanding beam exiting pinhole 106 is focused to a parallel beam by lens 108. (Lens 104, pinhole 106 and lens 108 constitute a spatial filter and beam expander.) The parallel, expanded beam passes through beamsplitter 112 and is deflected in the x-y plane by first scanning mirror 114, which rotates about an axis parallel to the z-direction. The beam then passes through a unitary telescope comprised of lenses 116 and 118 and is brought back as a parallel beam to the center of second scanning mirror 120, which rotates about an axis parallel to the x-direction and imparts a deflection in the y-z plane. Lenses 122 and 124, also comprising a unitary telescope, return the deflected beam to the center of beamsplitter 126, which is placed at the position of the entrance pupil of laser scan lens 128. Light reflected from beamsplitter 126 is focused to a diffraction-limited spot on specimen 130 by laser scan lens 128. The scan system is controlled electronically to produce a raster scan of the focus spot across the specimen. Light reflected from (or photoluminescence or fluorescence emitted by) specimen 130 is collected by laser scan lens 128 and impinges on beamsplitter 126. Light passing through beamsplitter 126 is collected by condenser lens 132 and falls on the active area of non-confocal detector 134. Condenser lens 132 and non-confocal detector 134 comprise a non-confocal detection arm. Light reflected by beamsplitter 126 passes back through the scan system, and part of this returning beam is reflected by beamsplitter 112 towards detector lens 136 which focuses the returning parallel beam onto confocal pinhole 138. Light passing through the confocal pinhole is detected by confocal detector 140. Detector lens 136, confocal pinhole 138 and confocal detector 140 comprise a confocal detection arm. A confocal image of the specimen can be recorded pixel-by-pixel by digitizing the signal from confocal detector 140 using a slow-scan frame grabber synchronized to the mirror scan system. A non-confocal image can be recorded by digitizing the signal froth detector 134. In this embodiment of the scanning beam imaging system, laser scan lens 128 is a telecentric F Theta lens. The image from detector 140 is confocal, because Pinhole 138 rejects all light in the returning beam which is not parallel to the axis as it enters lens 136, and thus rejects all light that does not originate at the focal point of laser scan lens 128. The image detected by detector 134 is not confocal, and if beamsplitter 126 is a dichroic beamsplitter, then detector 134 can be used to detect fluorescence or photoluminescence from the specimen 130, without the reduction in intensity caused by the passage of the returning beam back through the scan system. This system works well in recording confocal images in reflected light, but performance is not as good in fluorescence and photoluminescence imaging, or for non-confocal imaging in reflected light. The amount of light emitted from the specimen in fluorescence or photoluminescence is usually small, and only a small part of that is collected by laser scan lens 128, since Laser Scan Lenses have a much smaller Numerical Aperture (NA) than most objective lenses used for fluorescence microscopes. In addition, most Laser Scan Lenses are not colour corrected, and they often provide diffraction-limited performance at only one wavelength, as well as having large changes in focal length with changes in wavelength. Thus, although detector 140 works well in reflected-light confocal imaging, the signal is very weak in confocal fluorescence or photoluminescence imaging, except from the brightest specimens. Colour-corrected Laser Scan Lenses are available, but they are complicated and very expensive. When using detector 134 for non-confocal reflected-light imaging, reflections from the lens surfaces inside the laser scan lens result in flare that degrades the image. In confocal reflected-light imaging, the confocal pinhole 138 is very, effective at reducing flare, as well as rejecting any light returning from the specimen that does not originate at the focal point of laser scan lens 128.

Objects of the Invention

It is an object of this invention to provide a novel imaging or mapping system for macroscopic specimens. Both confocal and non-confocal detectors can be used if required. Several different contrast mechanisms may be used, including but not necessarily limited to the following: reflected light, transmitted light, photoluminescence (including spectrally-resolved photoluminescence), fluorescence (including spectrally-resolved fluorescence), fluorescence decay, scattered light, optical beam induced current or voltage, photoconductivity, scanning reflectance spectroscopy, photoreflectance spectroscopy, Raman effect imaging, and many others.

It is a further object of this invention to provide a novel photoluminescence imaging or mapping system for semiconductor specimens including wafers, epitaxial layers and devices made using compound semiconductors, porous silicon materials and devices, and other semiconductor materials and devices which photoluminesce when excited by laser radiation.

It is a further object of this invention to provide a novel fluorescence imaging or mapping system for biomedical specimens including fluorescent gels used in gene sequencing, and other biological or medical specimens that fluoresce when excited by laser radiation.

It is a further object of this invention to provide a novel fluorescence imaging or mapping system that can assist diagnosis of cancer by comparing the fluorescence emission of cancerous tissue with that of the surrounding normal tissue, or by combining imaging in fluorescence and/or reflected light with another contrast mechanism (for example Raman Effect) to aid diagnosis.

It is a further object of this invention to provide a novel imaging and digitization system for fingerprints, for recording latent prints (both untreated and treated with fluorescent dyes) and inked prints using reflected light and/or fluorescence as contrast mechanisms, and for in vivo detection of fingerprints with the finger pressed against a transparent sheet of glass or other transparent material.

It is a further object of this invention to provide an instrument in which a combination of measurements can be made on the same specimen, using the novel imaging or mapping system of this invention. Some of the many combinations are as follows: the combination of reflected light, photoluminescence and Optical Beam Induced Current imaging of semiconductors; the combination of reflected light, fluorescence, and Raman effect imaging of biomedical specimens. Measurements using different contrast mechanisms may be performed simultaneously, or sequentially, depending on the combination of measurements to be made.

BRIEF DESCRIPTION OF THE DRAWINGS

FIG. 2b shows a simplified side view of the laser scan lens, specimen and detector area of the imaging system of FIG. 2a.

DESCRIPTION OF THE INVENTION

The present invention is a practical scanning beam imaging system for macroscopic specimens (macroscope) that can form images using several different contrast mechanisms.

Figure 2A:
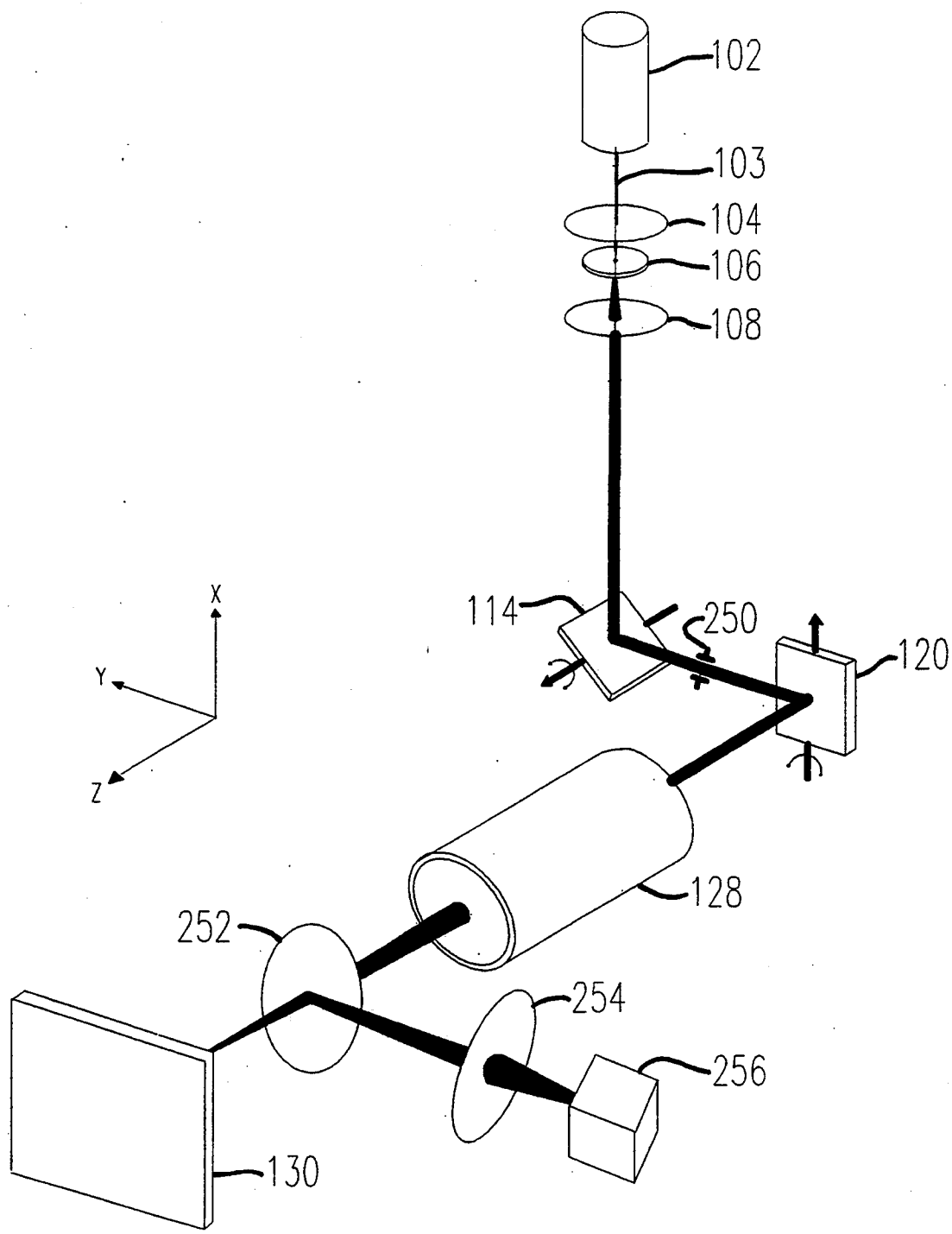
FIG. 2a shows a simplified perspective view of a preferred embodiment of the present invention, a scanning beam imaging or mapping system for non-confocal reflected-light, photoluminescence or fluorescence imaging.

FIG. 2a shows a first preferred embodiment of the invention, a simple non-confocal scanning laser imaging system. In this embodiment, light beam 103 from laser 102 (or other light source) is focused on pinhole 106 by lens 104. The expanding beam exiting pinhole 106 is focused to a parallel beam by lens 108. (Lens 104, pinhole 106 and lens 108 constitute a spatial filter and beam expander.) The beam expansion ratio is chosen so that the expanded laser beam fills entrance pupil 250 of laser scan lens 128. The parallel, expanded beam is deflected in the x-y plane by first scanning mirror 114, passes through the entrance pupil 250 of laser scan lens 128, and is deflected in the y-z plane by second scanning mirror 120. A raster scan is impressed on the laser beam by scanning mirrors 114 and 120. These two scanning mirrors are placed close together, on either side of the entrance pupil of the laser scan lens. Laser scan lens 128 focuses the beam through beamsplitter 252 to a spot on the specimen 130, and light reflected from (or emitted by) the specimen is partially reflected by beamsplitter 252 towards condenser lens 254, which is placed so that light collected from any position on the specimen falls on the active area of detector 256 as the scan proceeds. Condenser lens 254 and detector 256 comprise a non-confocal detection arm. This embodiment has several advantages over non-confocal versions of the prior art macroscopes which used the laser scan lens to collect reflected light from the specimen. First the numerical aperture (NA) of the condenser lens 254 is much larger than that of the laser scan lens, so a larger fraction of the light from the specimen is collected. Second, in the prior art macroscopes incoming laser light reflected back from the surfaces of the lens elements that make up the laser scan lens was detected by the non-confocal detector, and this caused a bright flare in the recorded image.

Figure 2B:
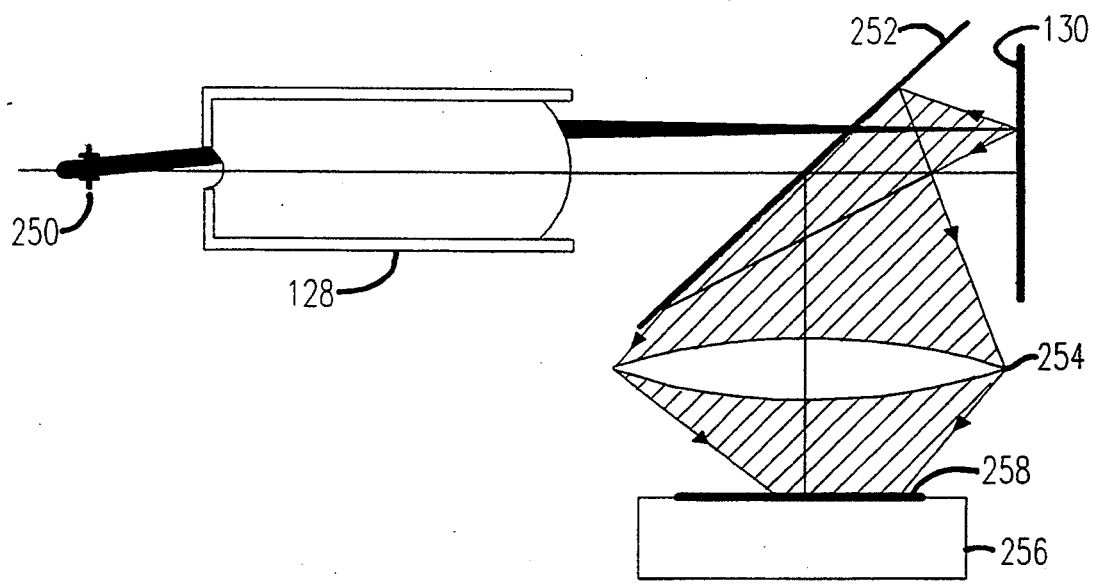

FIG. 2b shows a close-up view of the laser scan lens, specimen and detector area of the macroscope shown in FIG. 2a. The internal elements of the laser scan lens are not shown in this diagram, and the scan system is not shown The incoming laser beam, with scan impressed, is focused by laser scan lens 128 to a spot on specimen 130. A large cone of light (shown cross-hatched) reflected, scattered or emitted from the specimen is reflected (or partially reflected) by beamsplitter 252 towards condenser lens 254 which focuses the light into a converging beam which impinges on the active area 258 of detector 256. This diagram clearly shows the increased numerical aperture when condenser lens 254 is used to collect light from the specimen, instead of using the laser scan lens for this purpose. The advantage is even more apparent if a non-telecentric laser scan lens is used.

Figure 2C:
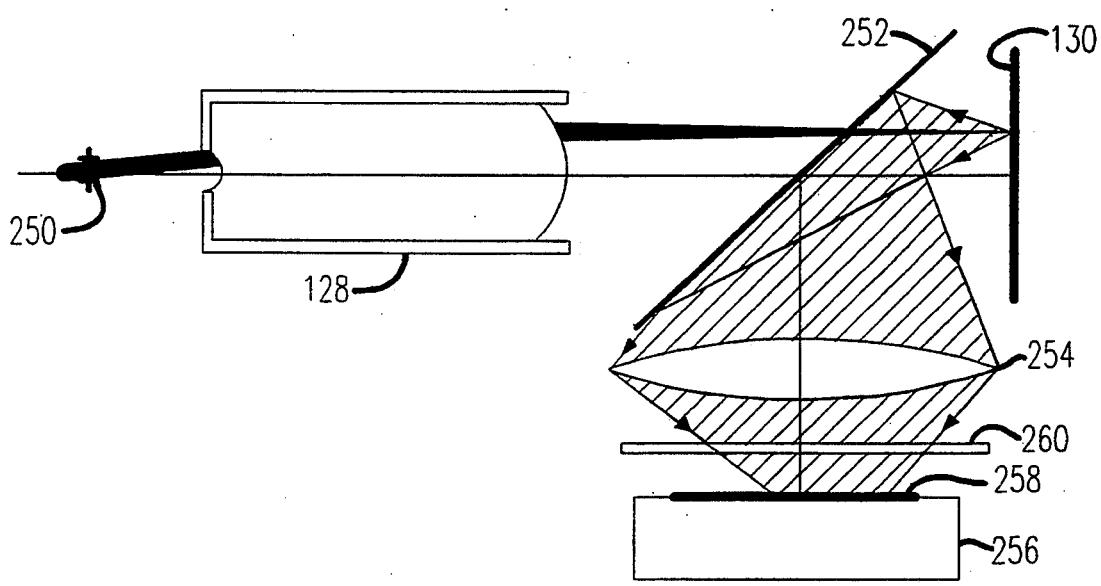
FIG. 2c shows the same area of the instrument as shown in FIG. 2b, with the addition of a narrow-band transmission filter for spectrally-resolved imaging.

When the macroscope of FIG. 2a is used tier fluorescence or photoluminescence imaging, a dichroic beamsplitter can be used as beamsplitter 252, which reflects the longer wavelength fluorescence or photoluminescence towards condenser lens 254 and detector 256. This is a particularly useful embodiment for non-confocal fluorescence (for example forming digital images of the fluorescent gels used in gene sequencing) and photoluminescence measurements, where signal strengths are often low, because the large NA in detection increases the fraction of light emitted from the specimen that will be detected. For spectrally-resolved detection, a spectrally-resolved detector can be used, or a narrow-band transmission filter 260 can be placed between condenser lens 254 and detector 256 (as shown in FIG. 2c), thus enabling the detector to detect only the narrow band of wavelengths transmitted by the filter. If a complete spectrum is required at every pixel position in the image, this can be accomplished in several different ways. For example, an active narrow-band transmission filter can be placed between condenser lens 254 and detector 256, and a complete raster-scan image can be acquired that includes only a narrow band of wavelengths around the selected wavelength. If a series of images are acquired at equally-spaced wavelengths, a three-dimensional data set in X, Y and Wavelength can be built up and stored in the computer. If only some characteristics of the spectrum are important at each pixel position (for example peak height, full width at half height, peak wavelength, distance between peaks, total emission at all wavelengths, etc.), then it may be appropriate to measure one scan line of complete spectra, by recording a series of scans across the same line on the specimen at equally-spaced wavelengths, computing and storing the important spectral characteristics at each pixel position in that scan line, and then move to the next scan line to repeat the operation. This is easy to accomplish in most scan systems, and it preserves the speed advantage of a scanning beam system while reducing the amount of data that must be stored for later computation.

Figure 2D:
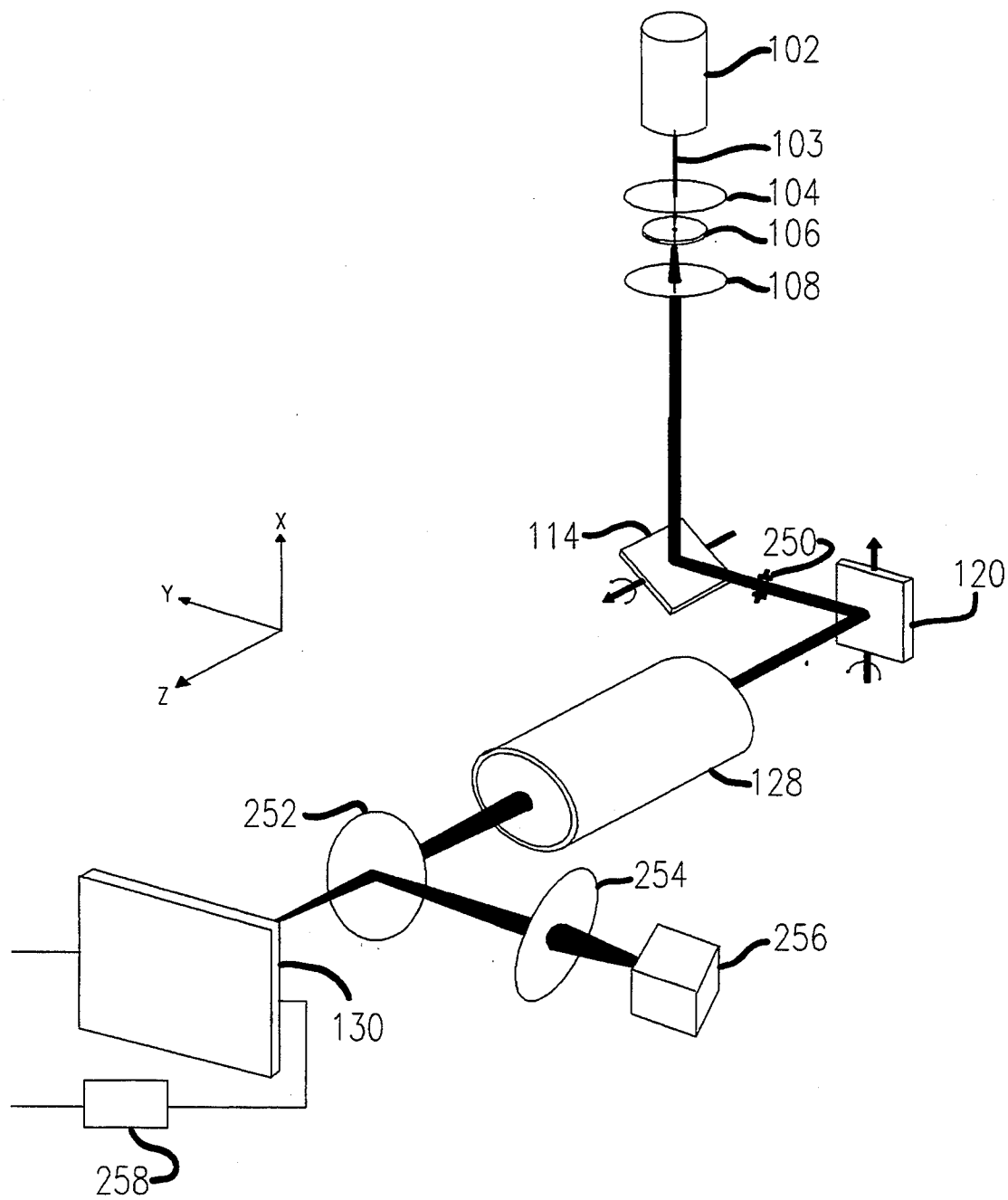
"FIG. 2d shows the imaging system of FIG. 2a, with the addition of an optical beam induced current detector."

The method and embodiment of the present invention just described will be important in photoluminescence mapping or scanning of semiconductor wafers, epitaxial layers and devices, where it is important to measure the photoluminescence spectrum at each pixel position, and to store and later map the changes in several spectral characteristics as a function of position across the specimen. The addition of a Optical Beam Induced Current detector 258, as shown in FIG. 2d, would allow the simultaneous measurement of this parameter, which is important in some specimens. The measurement of spatially- and spectrally-resolved photoluminescence can be combined with measurement of scattered light, reflected light, carrier lifetimes, photoreflectance, and many others.

Figure 1:
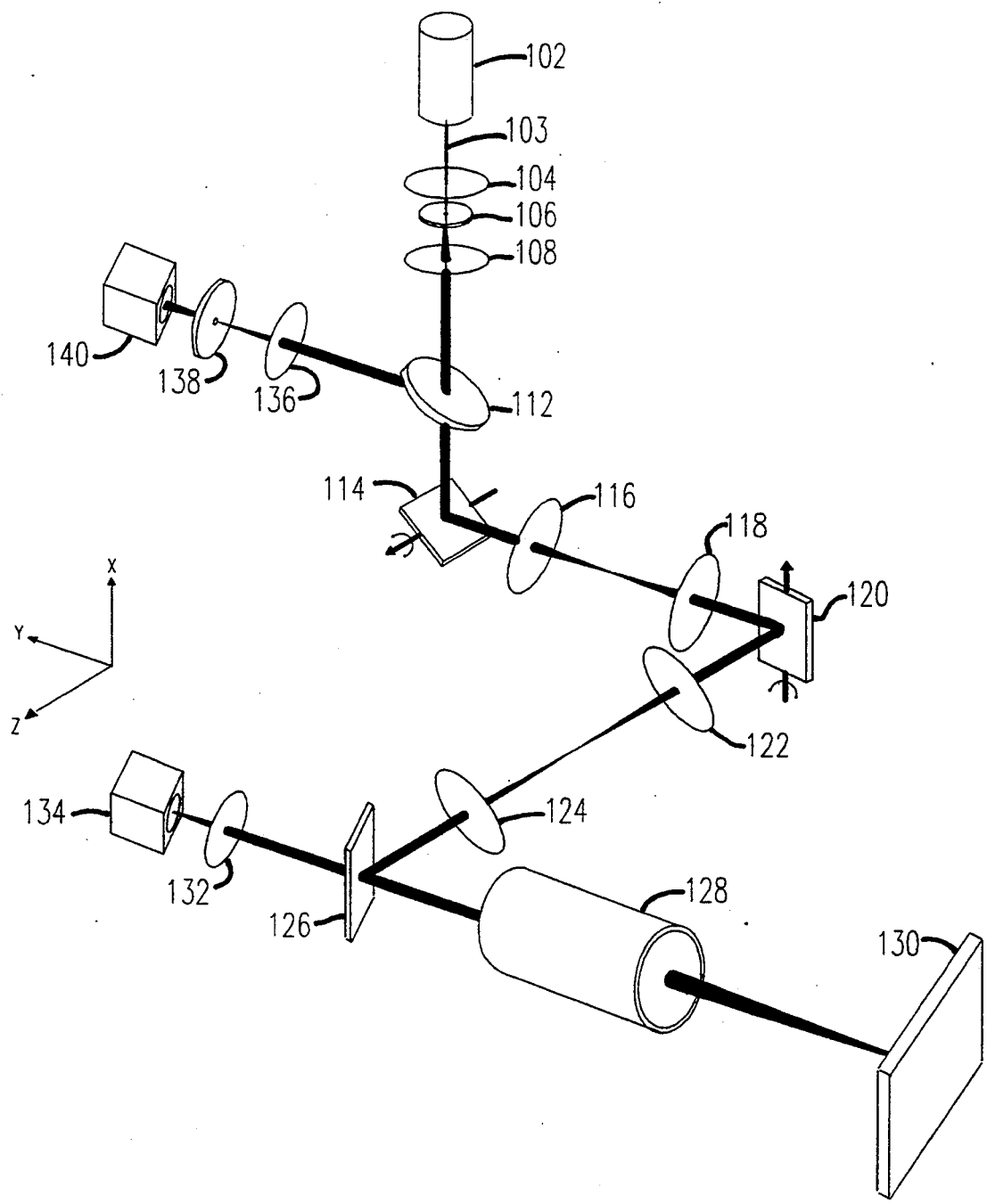
FIG. 1 shows a prior art confocal scanning beam laser imaging system with both confocal and non-confocal detectors.
Figure 3A:
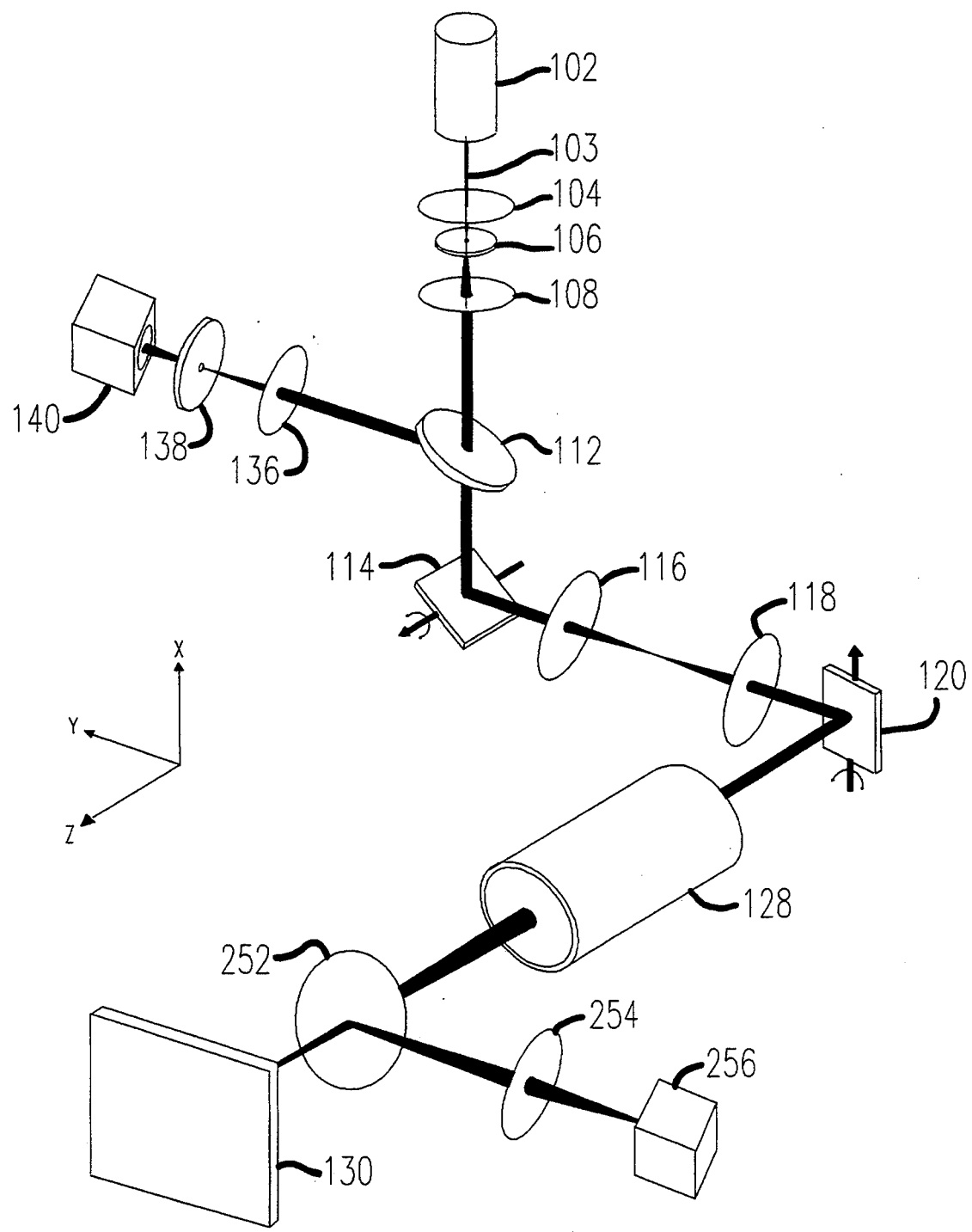
FIG. 3a shows a simplified perspective view of a preferred embodiment of the present invention that includes both confocal and non-confocal detectors "3b shows an embodiment of the present invention in which the scan system combines a beam scan in one direction with a stage scan in the other, perpendicular direction."

FIG. 3a shows a second preferred embodiment of the present invention, in which both confocal and non-confocal detection are implemented. After passing through the spatial filter and beam expander (comprised of lens 104, pinhole 106 and lens 108), the expanded laser beam 103 passes through beamsplitter 112 and is deflected in the x-y plane by first scanning mirror 114. A unitary telescope comprised of lens 116 and lens 118 brings the beam back to the center of second scanning mirror 120, which imparts a scan in the y-z plane. Scanning mirror 120 is placed at the position of the entrance pupil of laser scan lens 128. The beam, with raster scan impressed, is focused by laser scan lens 128 through beamsplitter 252 to a spot on specimen 130. Light reflected from (or emitted by) specimen 130 impinges on beamsplitter 252, where it is partially reflected and partially transmitted. The light reflected by beamsplitter 252 is collected by condenser lens 254, and is focused to a converging beam that impinges on the active area of detector 256. This detector can be used to detect non-confocal reflected-light images, or fluorescence or photoluminescence images, as disclosed in the first preferred embodiment of the present invention. Light from specimen 130 that passes through beamsplitter 252 is collected by laser scan lens 128, passes back through the scan system, whereby it's scan is removed, and is partially reflected by beamsplitter 112 towards lens 136, which focuses the parallel beam from the focus point on the specimen onto pinhole 138. Light passing through pinhole 138 is detected by confocal detector 140. This is an important embodiment of the present invention, because it allows both confocal and non-confocal images of the specimen to be recorded. It has two important advantages over the prior art system described in FIG. 1: First, since condenser lens 254 has a larger numerical aperture than laser scan lens 128, the non-confocal image from detector 256 is much brighter than that from detector 134 in the prior art imaging system. Second, part of the incoming laser beam is reflected from the lens elements of laser scan lens 128 back towards detector 134 in the prior art imaging system, causing a bright flare in the non-confocal image. Because detector 256 is placed after the laser scan lens, no such flare is seen in images recorded using detector 256.

Figure 3B:
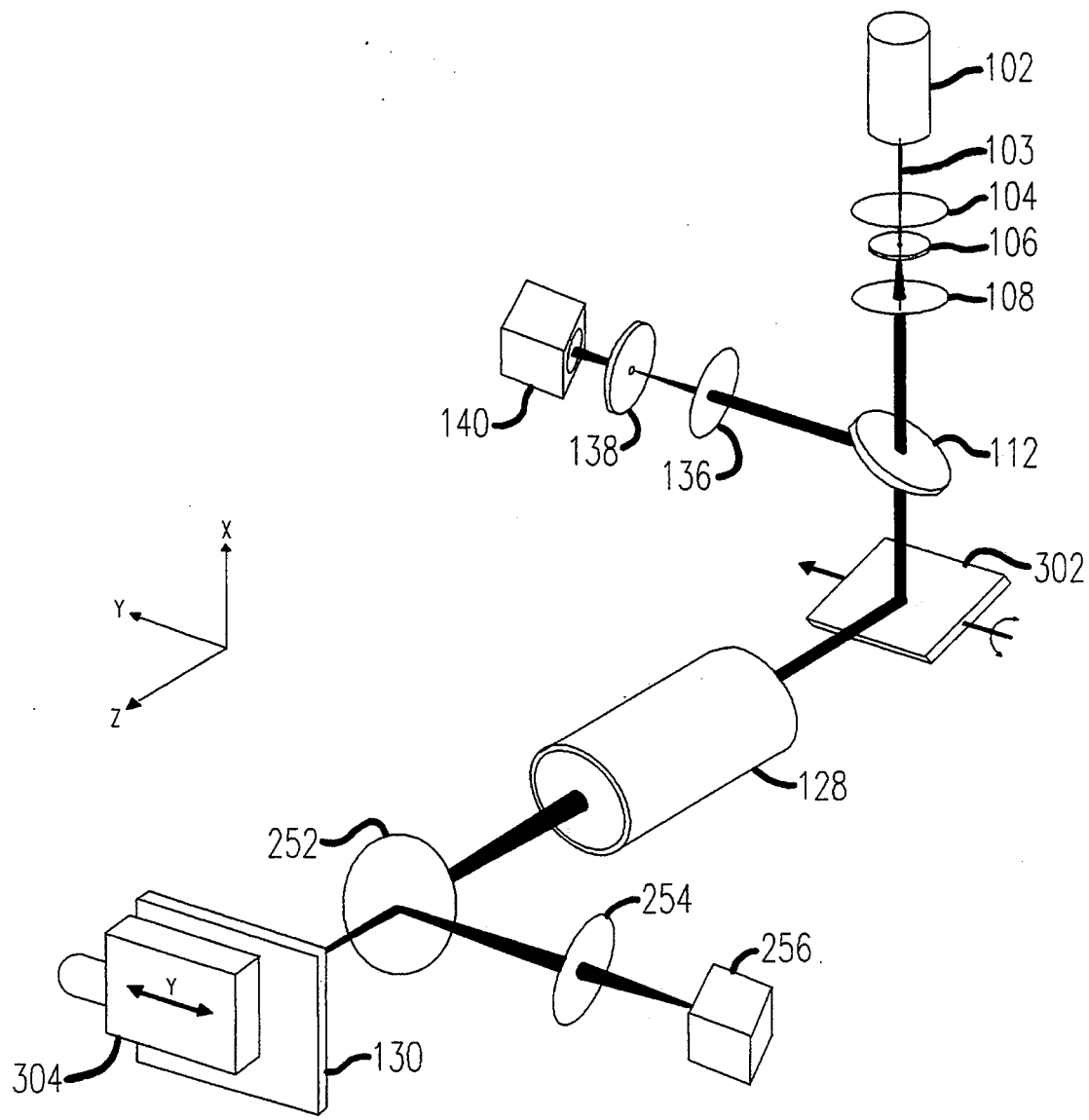

"FIG. 3b shows a third preferred embodiment of the present invention, in which a single scanning mirror 302 deflects the expanded laser beam 103 in the x-z plane, and specimen 130 is moved by a scanning specimen stage 304 in the y direction. This embodiment is particularly useful for very large specimens."

If beamsplitter 252 in FIG. 3a is replaced by a dichroic beamsplitter, then detector 256 can be used to collect fluorescence or photoluminescence from the specimen, while the reflected light, at the laser wavelength, passes back through the laser scan lens and scan system, is partially-reflected by beamsplitter 112, and is focused by lens 136 to pass through pinhole 138 and reach detector 140. This arrangement enables the imaging system to record a confocal image at the laser wavelength using detector 140, and to record a non-confocal fluorescence or photoluminescence image using detector 256. This is a very efficient embodiment for collecting light from the specimen, since the dichroic beamsplitter reflects virtually all oft he fluorescence or photoluminescence towards condenser lens 254 (which has a large numerical aperture) and detector 256, and transmits virtually all of the reflected light at the laser wavelength back toward detector 140. This embodiment has been found to be very useful for fingerprint detection, where both confocal reflected-light images and fluorescence images are often used.

Comments

1) Other light sources, including white light sources, may be used.

2) Because the scan described in FIG. 2a does not originate exactly at the entrance pupil of the laser scan lens, the scan on the specimen will be slightly nonlinear in this embodiment. The addition of lenses 116 and 118, as shown in FIG. 3a, will result in a linear scan, but the instrument is larger and more optical components are required, increasing cost.

3) Other scan systems, including rotating polygons, acousto-optic deflectors, etc. may be used. A scan system combining a beam scan in one direction with a stage scan in the other, perpendicular direction may also be used.

4) Designs that are not infinity-corrected are also possible.

5) All of the embodiments have been shown with a telecentric laser scan lens, however in some cases a non-telecentric scan lens can also be used.

6) Confocal fluorescence and photoluminescence imaging would be improved by using a colour-corrected telecentric laser scan lens.

Having described preferred embodiments of the new and improved scanning laser imaging or mapping system for macroscopic specimens, constructed in accordance with the present invention, it is believed that other modifications, variations, and changes will be suggested to those skilled in the art in view of the teachings set forth herein. It is therefore to be understood that all such variations, modifications and changes are believed to fall within the scope of the present invention as defined by the appended claims.

We claim:

1. A scanning-beam optical imaging system for macroscopic specimens comprising
    means for supporting a specimen to be observed and measured,
    an illumination source producing a light beam directed along an optical path toward said specimen,
    means for focusing the light beam to a spot in a prescribed specimen plane,
    means for scanning the light beam to move the spot in a predetermined scan pattern on said specimen plane,
    a detection arm receiving light reflected, scattered or emitted from said spot in said specimen plane comprising
        a condensing lens for collecting said reflected, scattered or emitted light,
        a detector placed behind said condensing lens, a beamsplitter directing light returning from said specimen into said detection
        arm, said beamsplitter placed between said focusing means and said specimen.

2. The imaging system of claim 1 wherein said means for focusing the light beam is an f*theta laser scan lens.

3. The imaging system of claim 2 wherein said beamsplitter is a dichroic beamsplitter, whereby light emitted from said specimen at wavelengths longer than that of said illumination source is reflected toward said detector, thus allowing photoluminescence or fluorescence images of said specimen to be recorded.

4. The imaging system of claim 3 wherein said detector is a spectrally-resolved detector, whereby spectrally-resolved fluorescence or photoluminescence images can be recorded.

5. The imaging system of claim 3 wherein said specimen is a semiconductor specimen, and further including an active filter placed in said detection arm in front of said detector, whereby spectrally- and spatially-resolved photoluminescence can be recorded from said semiconductor specimen.

6. The imaging system of claim 5 further including an optical beam induced current detector whereby photoluminescence and optical beam induced current can both be detected from said semiconductor specimen.

7. The imaging system of claim 3 wherein said specimen is a fluorescent gel, whereby large areas of the fluorescent gel can be accurately and rapidly scanned.

8. The imaging system of claim 7 wherein said means for scanning the light beam comprises a beam seam in one direction and a scanning specimen stage in the perpendicular direction, whereby very large specimens can be scanned rapidly.

9. A scanning-beam optical imaging system for macroscopic specimens comprising
    means for supporting a specimen to be observed and measured,
    an illumination source producing a light beam directed along an optical path toward said specimen,
    means for focusing the light beam to a diffraction-limited spot in a prescribed specimen plane,
    means for scanning the light beam to move said diffraction-limited spot in a predetermined scan pattern on said specimen plane,
    a first detection arm receiving light reflected, scattered or emitted from said diffraction-limited spot in said specimen plane comprising
        a condensing lens for collecting said reflected, scattered or emitted light,
        a first detector placed behind said condensing lens, whereby non-confocal data can be measured,
        a first beamsplitter directing light returning from said specimen into said first detection arm, said first beamsplitter placed between said focusing means and said specimen,
    a second detection arm receiving light reflected, scattered or emitted from said diffraction-limited spot in said specimen plane comprising
        a pinhole and a focusing lens for obtaining a focal point for confocal detection of the light returning from said specimen,
        a second detector placed behind said pinhole, whereby confocal image data can be measured,
        a second beamsplitter directing light returning from said specimen into said second detection arm, said second beamsplitter placed above said scanning means,
    whereby both confocal and non-confocal images of said specimen can be detected.

10. The imaging system of claim 9 wherein said means for focusing the light beam is a telecentric f*theta laser scan lens.

11. The imaging system of claim 10 wherein said first beamsplitter is a dichroic beamsplitter, whereby light emitted from said specimen at wavelengths longer than that of said illumination source is reflected toward said first detection arm, whereby non-confocal fluorescence or photoluminescence images of said specimen are recorded, and light reflected from said specimen at the same wavelength as that of said illumination source is reflected toward said second detection arm, whereby confocal reflected light images of said specimen are recorded.

12. The imaging system of claim 11 wherein said first detector is a spectrally-resolved detector, whereby spectrally-resolved fluorescence or photoluminescence images of said specimen are recorded.

13. The imaging system of claim 11 further including an active filter placed in said first detection arm in front of said first detector, whereby spectrally- and spatially-resolved fluorescence or photoluminescence can be recorded from said specimen.

14. The imaging system of claim 12 wherein said specimen is a semiconductor specimen and further comprising an optical beam induced current detector whereby photoluminescence and optical beam induced current can both be detected from said semiconductor specimen, in addition to confocal reflected-light imaging.

15. The imaging system of claim 13 wherein said specimen is a semiconductor specimen and further comprising an optical beam induced current detector whereby photoluminescence and optical beam induced current can both be detected from said semiconductor specimen, in addition to confocal reflected-light imaging.

16. The imaging system of claim 11 wherein said specimen is a fingerprint, whereby both fluorescence and confocal reflected-light images of said fingerprint are recorded.

17. A method for measuring and storing characteristics of spatially-resolved photoluminescence or fluorescence spectra comprising:

measuring one scan line with a complete spectrum at each pixel position, by recording a series of scans across the same line on the specimen at equally-spaced wavelengths, computing and storing the required characteristics of the spectrum at each pixel position in that scan line, moving to the next scan line to repeat the operation, until the required spectral characteristics have been measured, computed and stored for each pixel position in the image, whereby the amount of data that must be stored for later computation is reduced when compared to storing a series of complete images at each wavelength, the scan speed of a scanning beam system is preserved, and computation time can be further reduced by computing characteristics of the spectra for one scan line while measuring spectra for the next scan line.

* * * * *